United States Patent [19]

Garnier

[11] 4,351,614
[45] Sep. 28, 1982

[54] METHOD OF AND APPARATUS FOR CONTINUALLY MONITORING THE HEATING VALUE OF A FUEL GAS USING A COMBUSTIBILITY METER

[75] Inventor: John J. Garnier, Hales Corners, Wis.

[73] Assignee: Eaton Corporation, Cleveland, Ohio

[21] Appl. No.: 131,568

[22] Filed: Mar. 19, 1980

[51] Int. Cl.³ .............................................. G01N 25/54
[52] U.S. Cl. ........................................ 374/37; 73/1 G
[58] Field of Search .................... 73/190 CV, 191, 36, 73/190 R, 1 G

[56] References Cited

U.S. PATENT DOCUMENTS

| | | | |
|---|---|---|---|
| 1,205,704 | 11/1916 | Breyer | 73/190 CV |
| 2,052,181 | 8/1936 | Krogh | 73/190 G |
| 2,825,226 | 5/1958 | Daley, Jr. et al. | 73/190 CV |
| 3,095,728 | 7/1963 | Kindred et al. | 73/23.1 |
| 3,393,562 | 7/1968 | Breedlove | 73/190 CV |
| 3,777,562 | 12/1973 | Clingman, Jr. | 73/190 CV |
| 4,125,018 | 11/1978 | Clingman, Jr. | 73/190 CV |
| 4,140,004 | 2/1979 | Smith et al. | 73/36 X |
| 4,150,495 | 4/1979 | Stern | 73/1 G X |

Primary Examiner—Charles A. Ruehl
Attorney, Agent, or Firm—C. H. Grace; F. M. Sajovec

[57] ABSTRACT

A method of continually monitoring the heating value of a fuel gas, and the apparatus for carrying out this method. The method includes mixing a fuel gas of known heating value with a combustion-supporting gas, putting the mixture through a combustibility meter, adjusting the mixture to 100% or some fixed portion thereof of the lower explosive limit of the combustible gas, substituting a fuel gas of unknown heating value without changing the air to gas ratio and using the percent LEL now indicated by the combustibility meter to calculate the heating value of the unknown fuel gas. The apparatus for carrying out this method includes a combustibility meter (10) having a sensing transducer (12), a source of certified known fuel gas (30), a source of unknown sample fuel gas, a mixing system (14) for mixing these gases with air in controllable ratios, and an instrument (28) for recording the heating value of the unknown fuel gas.

13 Claims, 1 Drawing Figure

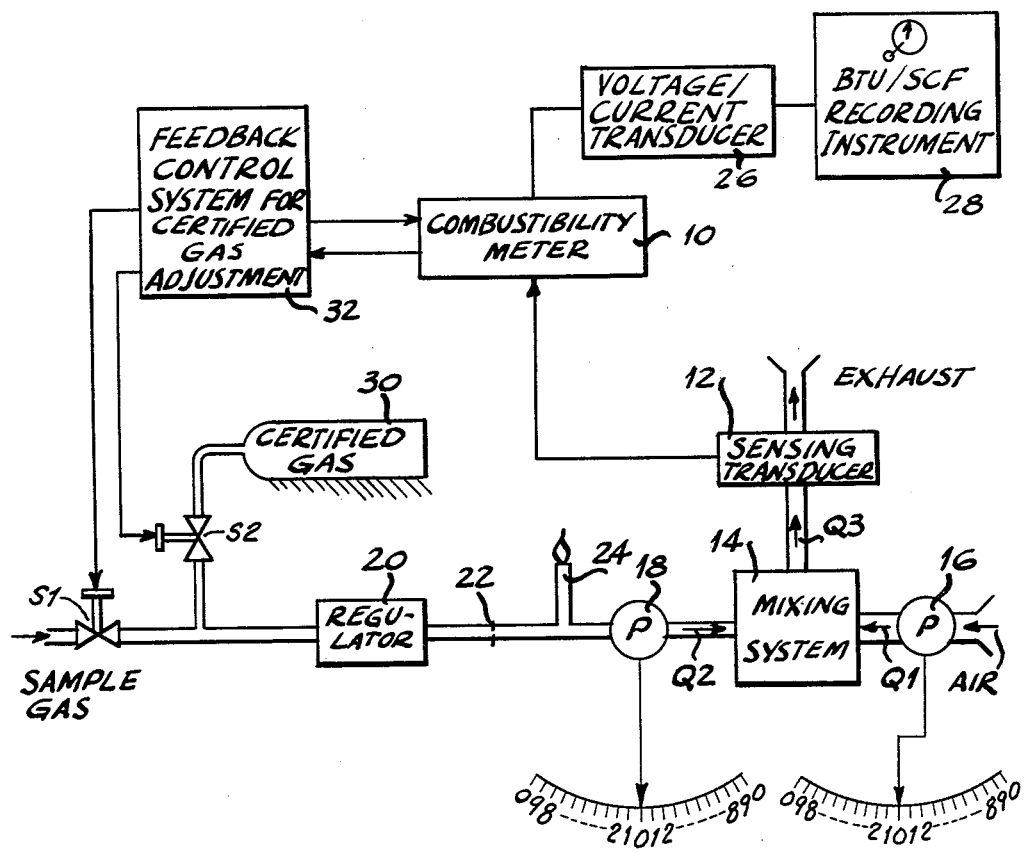

METHOD OF AND APPARATUS FOR CONTINUALLY MONITORING THE HEATING VALUE OF A FUEL GAS USING A COMBUSTIBILITY METER

BACKGROUND OF THE INVENTION

This invention relates to fuel gases and more specifically methods and apparatus for the continual monitoring of the heating value of these fuel gases.

The total heating value of a fuel gas is defined generally as the quantity of heat in British Thermal Units (BTUs) released when one standard cubic foot (SCF) of gas is completely oxidized, with both initial and final temperatures of all ingredients at 60° F. Thus, for example, if the gas is a hydrocarbon or a mixture of several hydrocarbons, the products of a complete oxidation with air are carbon dioxide, nitrogen and water vapor; when on SCF of the gas is mixed with sufficient oxygen to completely oxidize the gas, oxidation is carried out, and the products are cooled to 60° F., the total heat given off is the total heating value of the gas, in BTU/SCF.

Total heating value of a fuel gas, defined in this manner, is used extensively by gas utilities as a measure of the quality of a gas as fuel. If the total heating value is higher, fewer cubic feet of gas are needed to provide the same energy or work. Since the use of fuel gas is based on its heating value per unit volume, the charge for the fuel gas is determined on the same basis.

In addition, the proper operation of burners fed by gas is often extremely dependent upon heating value of the fuel gas. Thus it is important to be able to stabilize the heating value of the fuel gas. To do this, utilities need a method for continually monitoring the heating value.

One previous method for determining heating value involved burning the gas in an excess of oxygen, as for example in F. G. Breyer, U.S. Pat. No. 1,205,704, dated Nov. 21, 1916. Another method requires burning the gas in the exact proportion of oxygen which will bring the flame to its maximum temperature, as in W. H. Clingman, Jr., U.S. Pat. No. 3,777,562, dated Dec. 11, 1973. Since both of these methods involve burning of the gas, inlet conditions (i.e., temperature, pressure, etc.) must be carefully maintained in order to yield accurate readings. Small discrepancies in inlet conditions result in large errors in heating value measurement. Expensive equipment is necessary to correct for these small discrepancies.

SUMMARY OF THE INVENTION

The method of this invention involves the following basic steps:
1. Fuel gas of a known BTU content is mixed and diluted with air in a controlled ratio;
2. the mixture is fed into a combustibility meter;
3. the ratio of air to fuel gas in the mixture is varied until the combustibility meter indicates the the fuel gas is at, or at some set point below, its lower explosive limit (LEL);
4. the unknown fuel gas is then fed to the combustibility meter with the same controlled air-fuel gas ratio;
5. the percentage of LEL now indicated by the combustibility meter is used to calculate the heating value of the unknown fuel gas.

One object of this invention is to provide a method for determining heating value of a fuel gas which is lower in cost, with a faster response than previous methods.

Another object of this invention is to provide a method for continually monitoring heating value of a fuel gas which does not require that the total sample of fuel gas be burned in order to make the determination.

A further object of this invention is to provide a method for continually monitoring heating value of a fuel gas using a presently commercially available combustibility meter in the range at or below the lower explosive limit of the gas.

A more specific object of this invention is to provide a method for determining heating value of a fuel gas wherein the calibration point is at or below the LEL of the air-fuel gas ratio rather than any point in the explosive range of the fuel gas or above the upper explosive limit of the fuel gas.

Other objects and advantages of the invention will hereinafter appear.

DESCRIPTION OF THE DRAWING

The single FIGURE of the drawing is a diagrammatic view of an apparatus for carrying out the invention.

DESCRIPTION OF THE PREFERRED EMBODIMENT

Referring to the drawing, the apparatus for carrying out the method of this invention includes a presently commercially available combustibility meter 10 having a sensing transducer 12 in the stream of a mixture of combustible fuel gas and combustion-supporting gas. Hereinafter, combustible fuel gas and combustion-supporting gas will be termed "fuel gas" and "air" respectively, with the understanding that any suitable gas is included in these designations.

The mixture passes over transducer 12 after leaving the mixing system 14 at flow $Q_3$. Mixing system 14 can be any suitable system for the combining of two gases into one homogeneous mixture. The flow $Q_3$, is the sum of $Q_1$, the flow at which the air is pumped into the mixing system 14 by pump 16 and $Q_2$, the flow at which the fuel gas is pumped into the system by pump 18. The regulator 20, ballast orifice 22, and bleeder burner 24 are used simply to stabilize the inlet pressure at the inlet of pump 18 so that it is equivalent to atmospheric pressure, the inlet pressure at the air pump 16.

Since the inlet pressures to pumps 16 and 18 are equal as aforesaid, the ratio of the fuel gas to the air may be controlled in a conventional manner by selectively adjusting the pumping rates of pumps 16 and 18. For example, these pumps may be FMI (Fluid Metering, Inc.) Lab Pumps of the positive displacement, RR (rotating and reciprocating) piston type. As shown in the drawing, these pumps are provided with means for adjusting the stroke of the piston thereby to vary the pumping rate. This adjustment is controlled by moving a pointer on a bidirectional scale. If this pointer is adjusted on the right half of the scale, the pumping in one direction will be controlled. If this pointer is adjusted on the left half of the scale, the pumping in the other direction will be controlled. These two pumps are preferably run by a single motor of the instrumentation synchronous type having a double-ended shaft available from Bodine Electric Co., although alternatively the two pumps could be run by separate motors that are closely run at equal speeds by frequency control. An alternative known way to control the ratio of fuel gas to air is by use of two centrifugal blowers that have adjustable rates for moving the fuel gas and air into the mixing system.

Combustibility meters and their sensing transducer components are generally designed to be operated to continually monitor the percent of the lower explosive limit (LEL) of a fuel gas in air, usually for safety purposes, to prevent an explosion where a certain amount of explosive material (fuel gas) is expected to be in the air. In the case of Natural Gas, 100% of LEL means that the fuel gas diluted with air mixture is 6% fuel gas and 94% air, or one part fuel gas to 15.667 parts of air. A reading of 90% LEL means that the mixture is 5.4% fuel gas and 94.6% air.

While there are a number of commercially available combustibility meters and sensing transducers that can be used for elements 10 and 12 in this system, an example thereof is the Control Instrument corporation Model CCS Flammable Gas Detection Unit which includes a measurement and control module plus a sensor that continually samples the gas. Another example of such devices is a Robertshaw Controls Company Model 180 Combustible Gas Detector Transmitter and a Bacharach Instrument Company Combustible Gas Detector Sensor.

The heating value of the 6% mixture would also be 6% of the heating value of the undiluted fuel gas. Thus if the heating value of natural gas is assumed to be 1000 BTU/SCF, the heating value of the 100% LEL mixture is 60 BTU/SCF, and the heating value of the 90% LEL mixture is 54 BTU/SCF. Since the heating value of undiluted fuel gas is simply a multiple of the percent LEL and the air/fuel gas ratio, the output of the combustibility meter 10 passes through a voltage/current transducer 26 to the recording instrument 28 which records readings directly in BTU/SCF.

The method of this invention includes five steps. First, by closing valve S1 and opening valve S2 a certified known fuel gas 30 is mixed with air in the controlled flow ratio, $Q_1/Q_2$. Second, this mixture is fed into a combustibility meter 10. Third, the ratio of air to fuel gas, $Q_1/Q_2$, is set by varying the outputs of pumps 16 and 18 as hereinbefore described, until the combustibility meter indicates that the gas is at 100% LEL or at some fixed portion therebelow. Fourth, by opening valve S1 and closing valve S2 a sample of fuel gas, the heating value of which is not known, is now fed into the combustibility meter with the identical air to fuel gas ratio which produced the fixed percent LEL value using the certified known fuel gas. Fifth, the percentage of LEL now indicated by the combustibility meter is converted into the heating value of the unknown fuel gas by multiplying it by the constant K, where $$K = \frac{\text{Heating Value of Known Fuel Gas}}{\% \text{ LEL for Known Fuel Gas}}.$$

As a means of making the readings of heating value even more reliable a feedback control system for certified known fuel gas adjustment 32 is added. The function of this panel is to periodically turn off at solenoid valve S1 the sample unknown fuel gas being monitored, turn on at solenoid valve S2 the certified known fuel gas for a short period, approximately 10 to 20 seconds, readjust the combustibility meter to return it to the proper value for the certified known fuel gas, and by reclosing valve S2 and reopening valve S1 switch back to monitoring the sample unknown fuel gas. By this method the slow degradation of the sensing transducer element and other components of the combustibility meter can be accounted for.

A possible modification of the apparatus for carrying out this invention involves the substitution of a zero pressure regulator for the regulator 20 shown in FIG. 1. This substitution would obviate the bleeder burner 24 and the ballast orifice 22, both of which could then be eliminated. The purpose of the substitution, which would increase the total cost of the apparatus, is to more carefully regulate the inlet pressure at pump 18. Careful regulation of the inlet pressure allows more exact control of the outlet volumetric pumping capacity of the pump, and close regulation of outlet volumetric pumping capacities of pumps 16 and 18 is crucial to accurate measurement of heating value of either known or unknown fuel gas.

It is recognized that various modifications of the present invention are possible within the scope of the appended claims.

What is claimed is:

1. A method of continually monitoring the heating value of a fuel gas, comprising the steps of:
    mixing a fuel gas of known heating value with a combustion-supporting gas, in a controlled ratio, to make a homogeneous mixture;
    measuring the percent of lower explosive limit of said fuel gas;
    setting said ratio of fuel gas to combustion-supporting gas such that the ratio is 100% of the LEL of the fuel gas;
    substituting in said mixture a fuel gas of unknown heating value for said fuel gas of known heating value, without changing said ratio of fuel gas to combustion-supporting gas;
    and converting the resulting percent of LEL of said fuel gas of unknown heating value into the heating value of said fuel gas.

2. A method as recited in claim 1 wherein said combustion-supporting gas is air.

3. A method as recited in claim 1 wherein said percent of LEL of said gases is measured by feeding said fuel gases into a combustibility meter.

4. A method as recited in claim 1 wherein said controlled ratio of fuel gas of known heating value to combustion-supporting gas is set at a given level below 100% of the LEL of the fuel gas of known heating value.

5. A method as recited in claim 1 or claim 4 including periodically resubstituting said fuel gas of known heating value for said fuel gas of unknown heating value during a period of 10 to 20 seconds,
    and recalibrating said combustibility meter such that 100% LEL or said given level below 100%, is indicated by said meter during said period.

6. A method as recited in claim 1 wherein said conversion step is accomplished by multiplying the resulting percent of LEL by the heating value of the fuel gas of known heating value, and dividing the product by the percent of LEL of the fuel gas of known heating value.

7. An apparatus for continually monitoring the heating value of a fuel gas, comprising:
    a mixing system;

means for selectively feeding either fuel gas of known heating value or fuel gas of unknown heating value to said mixing system comprising:

a source of fuel gas of known heating value;

one or more sources of fuel gases of unknown heating values;

a first pump connected between said sources of fuel gases and said mixing system to force said fuel gases into said mixing system at a controlled rate;

and selectively controllable means for admitting first said known heating value fuel gas and thereafter one of said unknown heating value fuel gases to said first pump;

and means to control the ratio of the selected fuel gas and a combustion-supporting gas fed to said mixing system comprising:

a source of combustion-supporting gas;

a second pump to force said combustion-supporting gas into said mixing system at a controlled rate with respect to the controlled rate at which the selected fuel gas is fed thereto so as to provide a predetermined ratio thereof and such that said combustion-supporting gas is mixed with said selected fuel gas to provide a homogeneous mixture;

and a combustibility meter having a sensor located in the stream of said mixture leaving said mixing system such that the percent LEL of said mixtures having the known heating value fuel gas and the unknown heating value fuel gas are measured in sequence to determine the heating value of said unknown heating value fuel gas.

8. An apparatus as recited in claim 7, further comprising means connected between said sources of fuel gases and said first pump for regulating the pressures of said fuel gases at said pump.

9. An apparatus as recited in claim 8, further comprising means for recording the output of said combustibility meter over a period of time.

10. An apparatus as recited in claim 9, further comprising control means connected between said combustibility meter and said sources of fuel gases for periodically operating said selectively controllable means and resubstituting the fuel gas of known heating value in place of the fuel gas of unknown heating value for 10 to 20 seconds, and for recalibrating said combustibility meter such that 100% LEL or some fixed portion therebelow is indicated by said meter during said 10 to 20 seconds to provide a basis of comparison for said fuel gas of unknown heating value.

11. An apparatus as recited in claim 8 wherein said regulating means comprise a regulator, a ballast orifice and a bleeder burner.

12. An apparatus as recited in claim 8 wherein said regulating means comprise a zero pressure regulator.

13. An apparatus as recited in claim 9 wherein said recording means includes means for multiplying the percent of LEL shown by said combustibility meter by the heating value of the fuel gas of known heating value, and dividing the product by the percent of LEL of the fuel gas of known heating value, and wherein said recording means records said output of said combustibility meter only after said multiplication and division has been performed on said output.

* * * * *